United States Patent
Klootz

(10) Patent No.: US 6,799,878 B1
(45) Date of Patent: Oct. 5, 2004

(54) RECESSED INDEXING ROTARY MULTIPLE PORT TURRET FOR SINGLE OR MULTIPLE PORT MEDICAL FIBER-OPTIC ILLUMINATOR

(76) Inventor: Jack Klootz, 82 Erin Way, Naples, FL (US) 34119

( * ) Notice: Subject to any disclaimer, the term of this patent is extended or adjusted under 35 U.S.C. 154(b) by 225 days.

(21) Appl. No.: 10/063,961

(22) Filed: May 30, 2002

(51) Int. Cl.[7] .............................. F21V 7/04; G02B 6/04
(52) U.S. Cl. .................... 362/554; 362/26; 362/580; 362/274; 362/277; 362/283; 362/284; 362/324; 362/433
(58) Field of Search .................. 362/554, 26, 551, 362/572, 574, 580, 269, 271, 274, 277, 282, 283, 284, 322, 324, 433, 581

(56) References Cited

U.S. PATENT DOCUMENTS

| | | | |
|---|---|---|---|
| 4,786,127 A | * 11/1988 | Molnar | 385/52 |
| 5,309,330 A | * 5/1994 | Pillers et al. | 362/574 |
| 5,677,787 A | * 10/1997 | Copenhaver et al. | 359/350 |
| 5,882,102 A | * 3/1999 | Pileski | 362/554 |

* cited by examiner

*Primary Examiner*—Stephen Husar
*Assistant Examiner*—Sharon Payne
(74) *Attorney, Agent, or Firm*—Malin, Haley & DiMaggio, P.A.

(57) ABSTRACT

The present invention is a fiber-optic illuminator with a single or multiple internal turret used for connecting the illuminator with different fiber-optic cables. The internal turret may be incrementally rotated by a handle to present a customized predetermined port for a predetermined fiber-optic cable in optical communication with the light source. Incremental indexing rotation is accomplished through use of a biased bearing mechanism located inside the illuminator. The turret has cooling fins distant from the handle turned by the operator. The turret may carry a tubular lens for internal reflection of the illumination.

23 Claims, 7 Drawing Sheets

RECESSED INDEXING ROTARY MULTIPLE PORT TURRET FOR SINGLE OR MULTIPLE PORT MEDICAL FIBER-OPTIC ILLUMINATOR

BACKGROUND OF INVENTION

Field of Invention

This invention relates to a single or multiple port turret device for use with fiber-optic illuminators, and more specifically for a recessed rotary multiple port turret device for mounting within an illuminator and for operatively connecting to one of a variety of different size headlight or endoscopic fiber-optic cables or cable with differing fiber-optic cable connection mechanisms in order to allow light from the illuminator to pass therethrough.

Many surgical applications today use fiber-optic illuminator devices to provide light upon the surgical subject and the surgical area. Particularly, illuminator devices provide the necessary lighting for surgical headlamps and rigid or flexible endoscopes.

Traditionally, a manufacturer's illuminator is designed to be compatible only with that manufacturer's fiber-optic cable. Other fiber-optic cable designs, exhibiting different thicknesses and shapes cannot fit into the existing port of the manufacturer's illuminator. Most illuminators cannot accept cables produced by competitors. As a result, hospitals and clinics have often been limited to using illuminators and cables manufactured by the same company. Replacement cables from another company cannot be used unless a corresponding illuminator is on hand. This can present an expensive and inefficient dilemma for the institution. While a rotary turret that attaches to the outside of the illuminator is currently available, such as the inventor's exterior turret in his U.S. Pat. No. 5,617,302. However, this device requiring mounting a piece on an existing illuminator. The exterior indexing rotary turret also provides less secure connection with the fiber-optic cable, which may create a dangerous situation in the middle of a surgical operation. Moreover, some illuminators may not be built to provide a mounting area for an illuminator. In addition, since the cooling fins on the prior art exterior turret are on the portion of the turret handled by the operator, the operator is in danger of being burned by the turret.

Conventional fiber-optic illuminators exhibit a number of problems in addition to the lack of interchangeable parts. For example, the jack or port that accepts the proximal connector of the fiber-optic cable is typically located close to the internal lamp or light source within the illuminator. As a result, the area surrounding the port tends to become very hot and difficult, if not impossible to handle even when not using inventor's exterior turret.

Lack of secure engagement between the fiber-optic proximal connector and the illuminator has also been a problem. During use the cable has a tendency to become loose from the illuminator. This can disrupt the medical or surgical procedure for which the illuminator is being used. Moreover, conventional turrets are often difficult to rotate and require varying degrees of torque. As a result, indexing cannot be performed in an optimally smooth, quick and convenient manner. Another drawback with the existing turrets is that they are difficult to manufacture and install, making them highly expensive.

An additional drawback with existing fiber-optic illuminators is that since the port or jack that accepts the fiber-optic cable is mounted upon the outside of the illuminator and often protrudes several inches from the side of the illuminator, the likelihood of damage to the port or jack is increased, due to the movement of the user during surgical or diagnostic procedures. Furthermore, if an external turret is used on a fiber-optic illuminator, then it is awkward, if not impossible, to use a fiber-optic cable that requires the illumination to be manipulated by a tubular lens before entering the cable.

Accordingly, what is needed in the art is an internal rotary indexing port turret mechanism for use with fiber-optic cable illuminators that accepts one of a variety of different fiber-optic cable designs and sizes and wherein the turret mechanism is mounted within the illuminator thereby eliminating damage that might occur to the turret mechanism if mounted upon the outside of the illuminator. What is also needed is an illuminator that can easily accept fiber-optic cables from several manufacturers without mounting extraneous hardware. What is also needed is a rotary indexing port mechanism that may be turned while minimizing the risk of burning the operator's hand.

It is, therefore, to the effective resolution of the aforementioned problems and shortcomings of the prior art that the present invention is directed.

However, in view of the prior art in at the time the present invention was made, it was not obvious to those of ordinary skill in the pertinent art how the identified needs could be fulfilled.

SUMMARY OF INVENTION

The present invention comprises a turret for interconnecting a fiber-optic illuminator having a light source and a fiber-optic cable for use within a housing for the fiber-optic illuminator. The indexing rotary turret has a generally cylindrical body portion having a plurality of ports wherein each port is adapted for inter-engagement with a fiber-optic cable. The invention includes means for incrementally rotating and indexing the body portion within the housing of the fiber-optic illuminator so that a particular port is in optical communication with the light source. To cool the turret are one or more cooling fins located around each turret port, preventing overheating of the turret.

The turret has a stand axis and a handle stand axis, and is located within the illuminator between a stand and a front panel of the illuminator. The turret further includes a handle located outside the housing connected to the body portion of the turret at the handle axis.

In a preferred embodiment, the indexing rotary turret is incrementally turned using a disk including a plurality of depressions on the back surface located at the back end of the turret body each adapted to receive a resilient biased bearing located within the housing of the fiber-optic illuminator and means for attaching the disk to the rear portion of the turret body.

In an alternative embodiment, the means for incrementally rotating the body portion includes a plurality of depressions on the back end of the turret body itself, and each depression is adapted to receive a resilient biased bearing located within the housing of the fiber-optic illuminator.

In another alternative embodiment, at least one cooling fin has a cleft, a tubular lens within the cleft and means for securing the tubular lens within the cleft.

In yet another alternative embodiment, the port further includes a spring adapted for linkage to a specific fiber-optic cable.

The invention is also an entire fiber-optic illuminator, including a light source, an indexing rotary turret comprising a plurality of ports each with a front end and a back end wherein the front end of each port is specifically adapted for inter-engagement with a fiber-optic cable, a housing that at least partially encloses the light source and the turret body, and means for rotatably mounting the turret within the housing such that a particular port simultaneously is in optical communication with the light source and is accessible from outside the housing. It is preferred that the illuminator also has a handle located outside the housing connected to a front end of the turret.

In the illuminator, it is preferred that the rotary indexing turret includes a disk having a plurality of depressions on the back surface located at the rear portion of the turret whereby each depression is adapted to receive a resilient biased bearing within the housing of the fiber-optic illuminator and means for attaching the disk to the rear portion of the turret body. Alternatively, there are a plurality of depressions on the back end of the turret body whereby each depression is adapted to receive a resilient biased bearing located within the housing of the fiber-optic illuminator.

In the preferred embodiment, the housing holds a stand for the turret located inside the housing. The stand preferably has a depression, a bearing located in the depression and a resilient spring biasing the bearing into mechanical cooperation with the turret so that the turret is incrementally rotatable.

In another alternative embodiment, the invention is a recessed rotary indexing multiple port turret mechanism for mounting within a fiber-optic illumination device, including a turret body adapted for mounting within said fiber-optic illumination device, said turret body comprising a base portion and an elongated portion, said base portion including one or more ports sized to selectively receive and engage an end of one of a multiple of fiber-optic cables, said elongated portion including one or more longitudinal ports disposed there through, said one or more longitudinal ports corresponding to said one or more ports in said base portion, said one or more longitudinal ports sized to receive and engage said one end of said variety of fiber-optic cables, a mount for the turret body inside the illumination device and means for selectively controlling the rotation of said turret body in order to expose one of said turret body ports such that light from said illumination device is directed through a corresponding fiber-optic cable engaged with said exposed port.

In an alternative embodiment, the elongated portion further comprises a plurality of cooling fins longitudinally disposed there through. Preferably, in the recessed rotary multiple port turret mechanism each said port is comprised of a predetermined shape. In still another alternative embodiment, each said port is adapted for a different fiber-optic cable.

It is therefore an object of the present invention to provide a multiple port mechanism for use inside a fiber-optic illuminator where it can be protected from the elements.

It is a further object of the invention to provide an internal turret that accomplishes improved interconnection between an illuminator and a fiber-optic light source.

It is a further object of this invention to provide an internal rotary indexing turret for a fiber-optic light source that minimizes the risk of burns to an operator.

It is a further object of the invention to provide an internal rotary indexing turret in which cooling fins are located far from the handle used by an operator.

It is a further object of the invention to provide a fiber-optic illuminator that is capable of interconnecting to several different types of headlights and endoscopic fiber-optic cables without needing additional adapting pieces to be mounted to it.

It is a further object of the invention to provide an internal indexing rotary turret that is relatively easy and economical to manufacture.

It is another object of the present invention to provide an internal turret that may fit a fiber-optic cable that requires an internal tubular lens.

It is to be understood that both the foregoing general description and the following detailed description are explanatory and are not restrictive of the invention as claimed. The accompanying drawings, which are incorporated in and constitute part of the specification, illustrate embodiments of the present invention and together with the general description, serve to explain principles of the present invention.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 2A is an exploded rear view of the invention.

DETAILED DESCRIPTION

Figure 1:
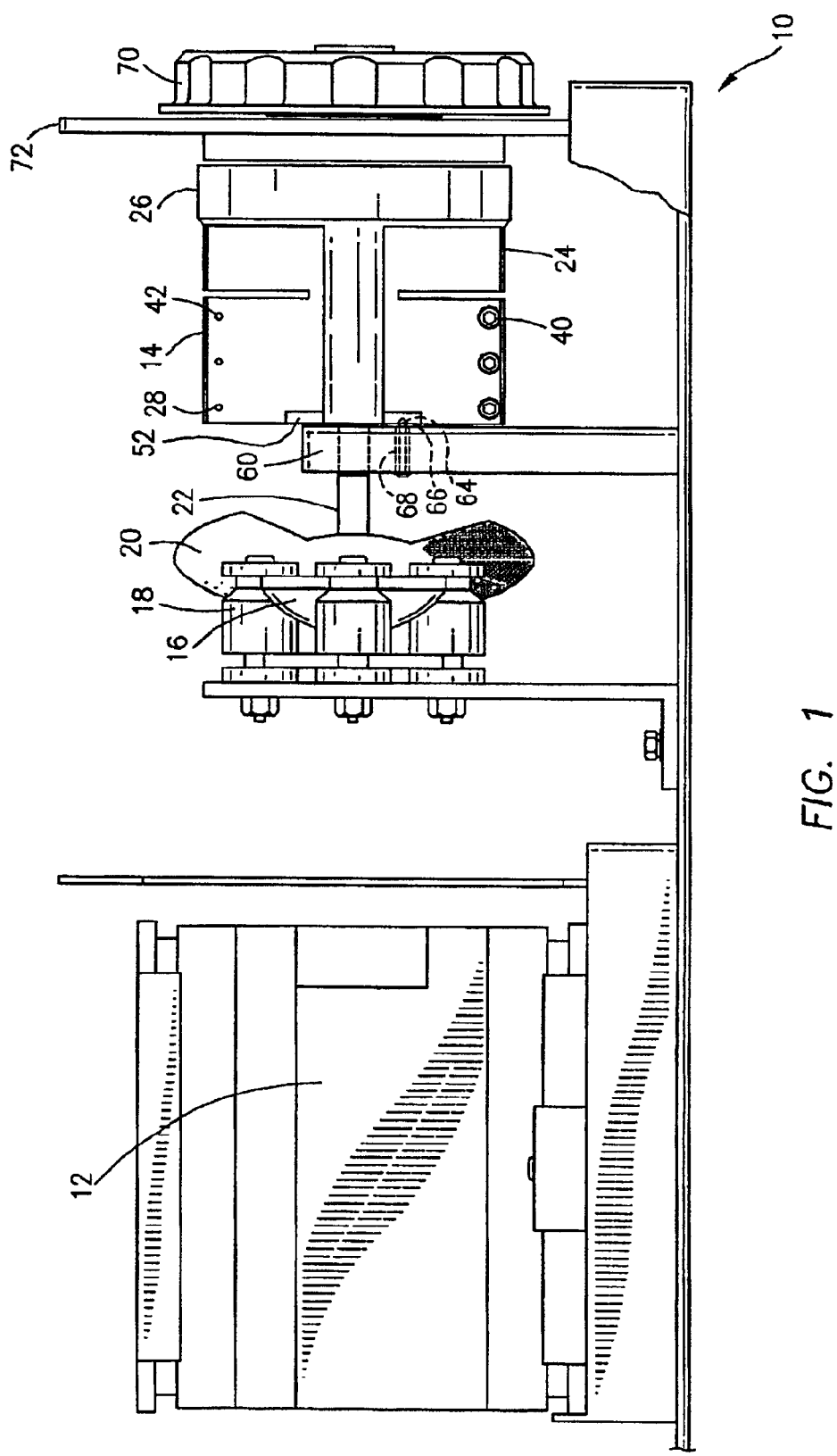
FIG. 1 is a cutaway side view of the turret of the invention.

FIG. 1 shows the inventive fiber-optic illuminator generally at 10. The illuminator comprises a light source 12. Preferably the light source is a xenon light source, although other sources such as metal halite are known in the art and may be used. It is preferred that the light source 12 emits light that is focused by a lens 16 held by a lens holder 18. Preferably, the lens holder 18 is attached to the bottom inside surface of the illuminator 10. The light emitted from the light source 12 may be diffused by a diffuser-screen 20 that is attached to a diffuser stem 22 that is offset from the emissions of the light source 12. The light enters a cylindrical turret body 24. Preferably, the turret body 24 is in rotatable contact with a turret stand 60, and lies between the turret stand 60 and the front wall 72 of the illuminator 10.

Figure 2:
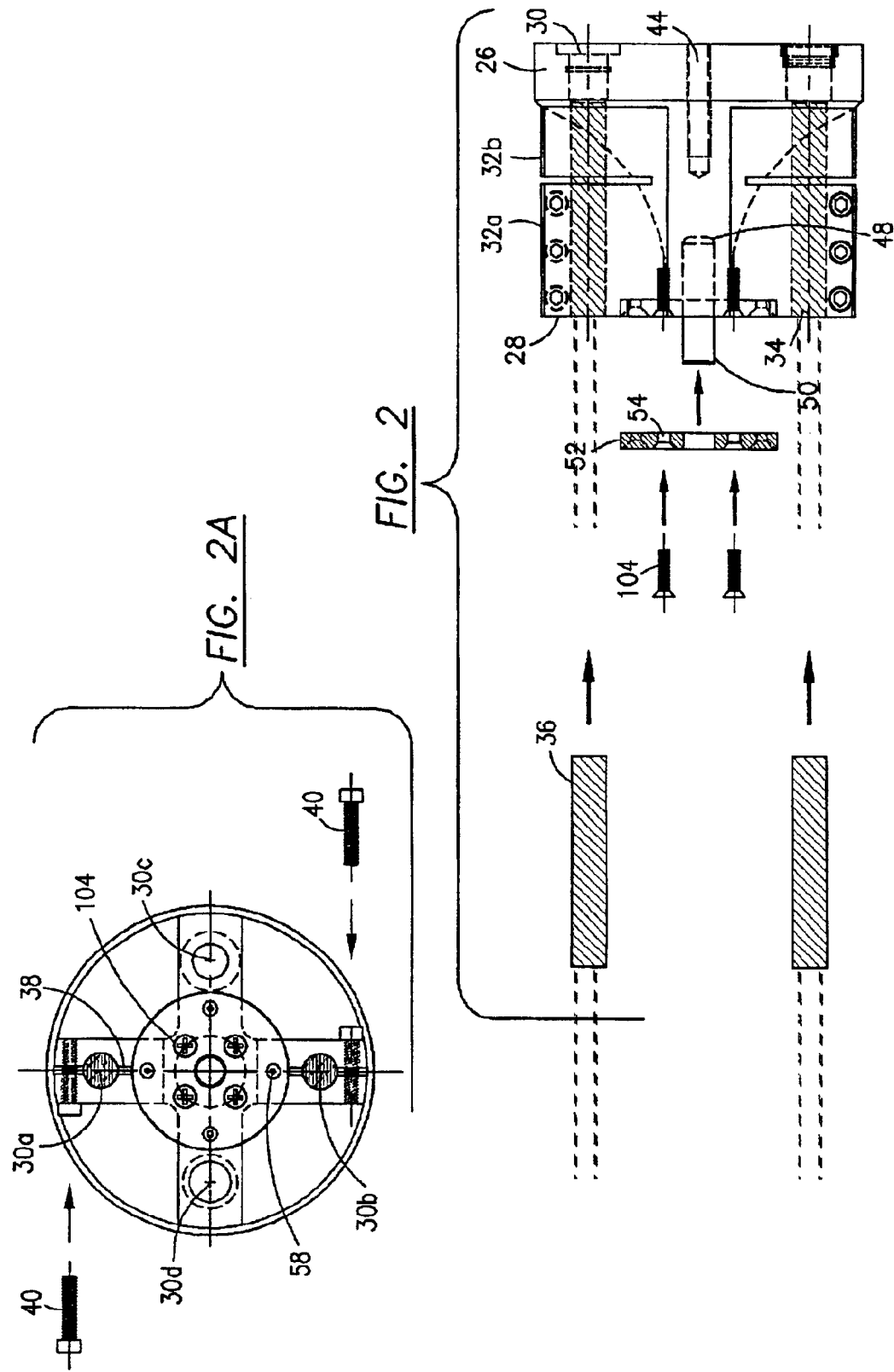
FIG. 2 is a cutaway exploded side view of the invention.
Figure 3:
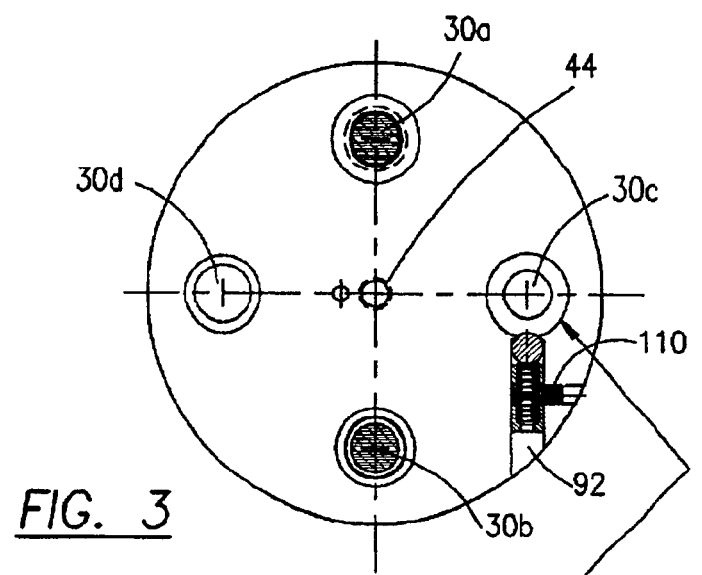
FIG. 3 is a cutaway front view of the invention.
Figure 3A:
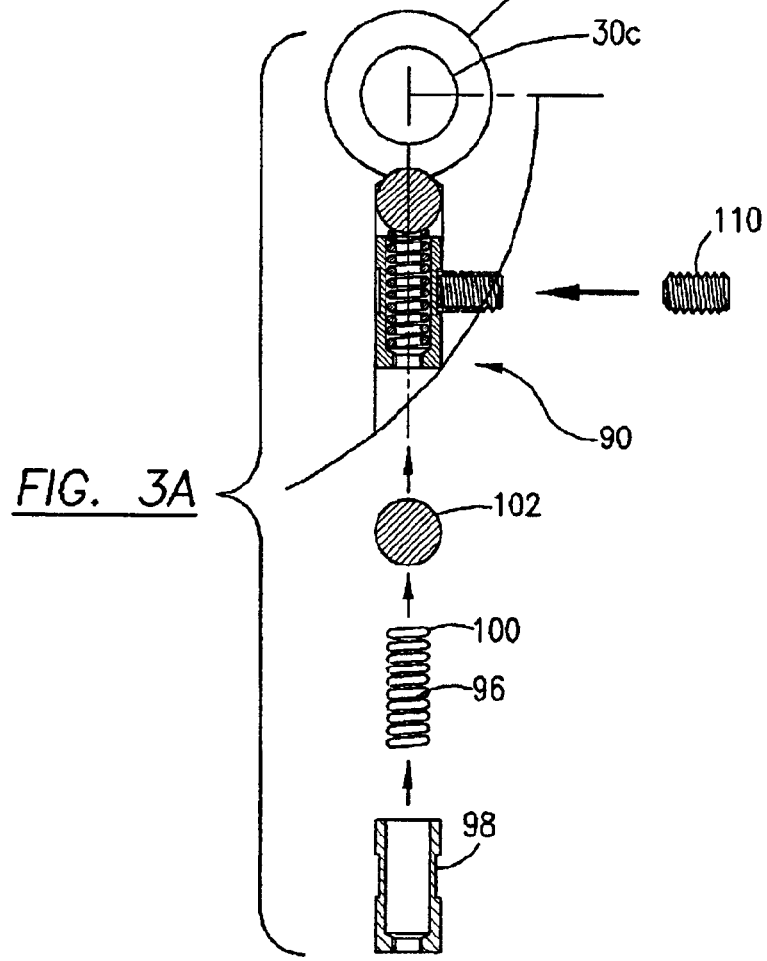
FIG. 3A is an close up sectional view of a portion of the cutaway front view of FIG. 3.
Figure 6:
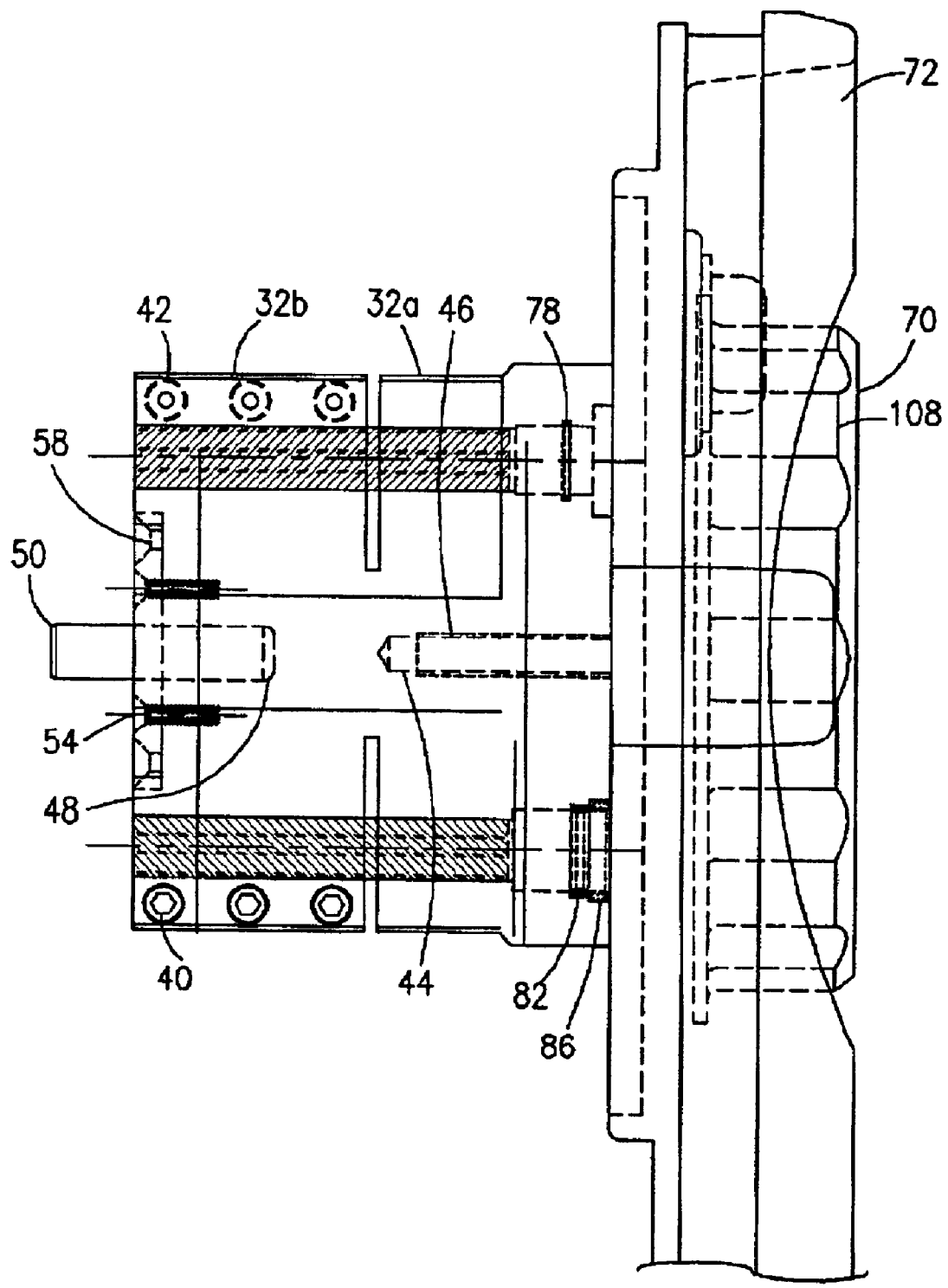
FIG. 6 is a cutaway side view of a detail of the inventive illuminator.
Figure 7A:
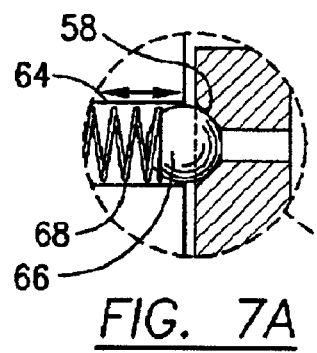
FIG. 7A is a cross section of a detail of the disk of the preferred embodiment of the invention.
Figure 7:
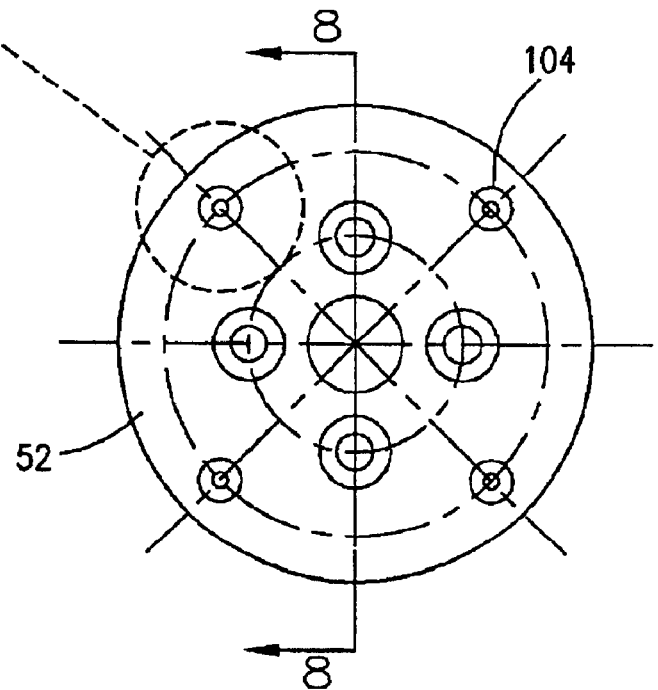
FIG. 7 is a top view of the disk of the preferred embodiment of the invention.
Figure 8:
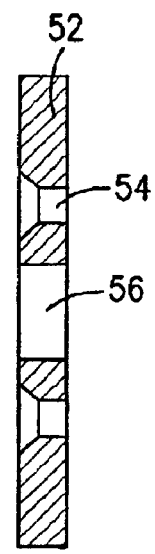
FIG. 8 is a cross section of the disk of the preferred embodiment of the invention.

The cylindrical turret body 24 is shown in detail in FIGS. 2, 2A and 6. Preferably the turret body is made of a rigid material, such as stainless steel or aluminum. The turret body 24 has a front end 26 and a back end 28. The turret body 24 has a plurality of port cavities 30 on the front end 26. Each port cavity 30 is in communication with a corresponding light channel 34 on the back end 28 of the turret body 24. The port cavities 30 and the light channels 34 are located around the central axis of the turret body. The turret body 24 is capable of being incrementally rotated so that a specified port cavity 30 and corresponding light channel 34 is in communication with the light source 12. In the preferred embodiment, each light channel 34 has a cooling fin 32 surrounding it to help dissipate the heat from the light source 12.

It may be preferred for use with some fiber-optic cables to be used with the illuminator 10 that the light from the light source 12 is magnified, focused or otherwise manipulated before it enters a port cavity 30. The light channel 34 may further comprise a tubular lens 36 placed within the path of the light emitted by the light source 12. The tubular lens 36 is preferred to be a cladded fiber-optic rod lens to promote internal reflection of light emitted from the light source. Preferably, to secure the tubular lens 36 within the light channel 34, the light channel 34 is constructed with a cleft 38 in the cooling fin 23. After the tubular lens 36 is placed in the light channel 34, it is secured in place with one or more lens securing screws 40 located in one or more appropriate holes 42 for the securing screws 40 located through the cooling fin 23. Preferably the securing screws 40 are made from a rigid material such as stainless steel or aluminum. Although three such screws are shown per cleft 38, more or less securing screws 40 may be used so long as they secure the tubular lens 36 within the light channel 34. Other equivalent means for securing the tubular lens 36, either permanently or temporarily, may be used and are well known in the art.

It is also preferred that the turret body 24 also comprises a handle axis 46. Preferably, a recess 44 for the handle axis 46 is formed into the front end 26 of the turret body 24, and the handle axis 46 is press fit into the recess 44. However, other methods of having a handle axis 46 on the turret body 24 may be used and are known in the art. In addition, the handle axis 46 may be formed as an intrinsic part of the turret body 24.

It is also preferred that the turret body 24 comprises a stand axis 50 located on the back end 28 of the turret body. Like the handle axis 46, it is preferred that a recess 48 for the stand axis 48 is formed into the back end 28 of the turret body 24. The stand axis 50 is then press fit into the recess 48. As is the case for the handle axis 46, other methods of having a stand axis 50 on the turret body 24 may be used and are known in the art. In addition, the stand axis 46 may be formed as an intrinsic part of the turret body 24. Preferably, the turret body 24 is mounted within the illuminator 10 so that it is incrementally rotatable on its stand axis 50 and its handle axis 46.

For the incrementally rotating the light channels 34, in the preferred embodiment the turret 14 comprises a separate disk 52, as shown in FIGS. 2, 4, 7, 7A & 8. It is preferred that the disk 52 is made from a rigid material such as stainless steel or aluminum. The disk 52 is secured to the back end 28 of the turret body 24, preferably in a pre-formed corresponding groove in the back end 28 of the turret body 24. The disk 52 includes a central void 56 for the stand axis 48 to pass through. The disk 52 is preferably secured to the back end 28 of the turret body 24 by one or more disk screws 104 fitted through corresponding one or more disk screw holes 54 and into the back end 28 of the turret body 24. However, the disk 52 may be secured by other means known in the art, such as an adhesive. The disk 52 comprises a plurality of depressions 58 on the back side of the disk 52 appropriate for a resilient bearing mechanism. As shown, the depressions 58 are formed completely through the disk 52. However, the depressions 58 may be formed only onto the back surface of the disk 52. Alternatively, the turret body 24 may be formed so that the appropriate depressions are formed on the turret body 24 itself, thereby obviating the need for the disk 52.

The turret 14 is in contact with a stand 60 within the illuminator 10, as shown in FIG. 1. The stand 60 comprises a recess 62 open toward the turret body 24 which is complementary to the stand axis 50 and allows the turret body 24 to be rotated. Alternatively, the recess 62 may go completely through the stand 60. In another alternative, the stand axis 50 is rotatably secured to the stand 60 by a flanged portion located on the back end of the stand axis 50. This flanged portion may be intrinsically formed onto the stand axis 50 or may be attached to the stand axis 50 after the stand axis 50 is formed.

As shown in FIG. 1, the stand 60 further comprises at least one recess 64 appropriate for a mechanism to allow the turret body 24 to be incrementally rotated, such as a biased bearing mechanism. Within the recess 64 is a biasing means for biasing a bearing outwardly from the depression, such as a spring 68. The spring 68 biases a bearing 66 against appropriate depressions 58 in the disk 52, or, in the alternative embodiment, in the back end 28 of the turret body 24. Thus, as the turret body 24 is rotated, the biased bearing 66 allows the turret body 24 to be incrementally rotated. Although other equivalent means for incrementally rotating the turret body 24 are known in the art, the illustrated method is the best one known to the inventor. Furthermore, more than one biased bearing mechanism may be used within a separate other recess or a connected recess in the stand 60.

Figure 5:
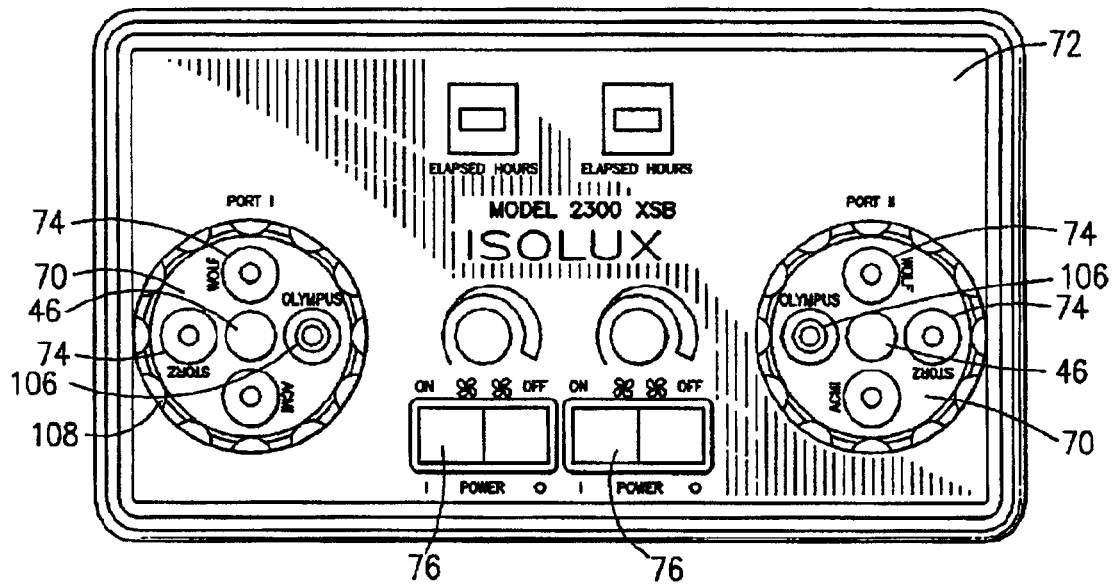
FIG. 5 is a front view of an alternative embodiment of the invention.
Figure 5A:
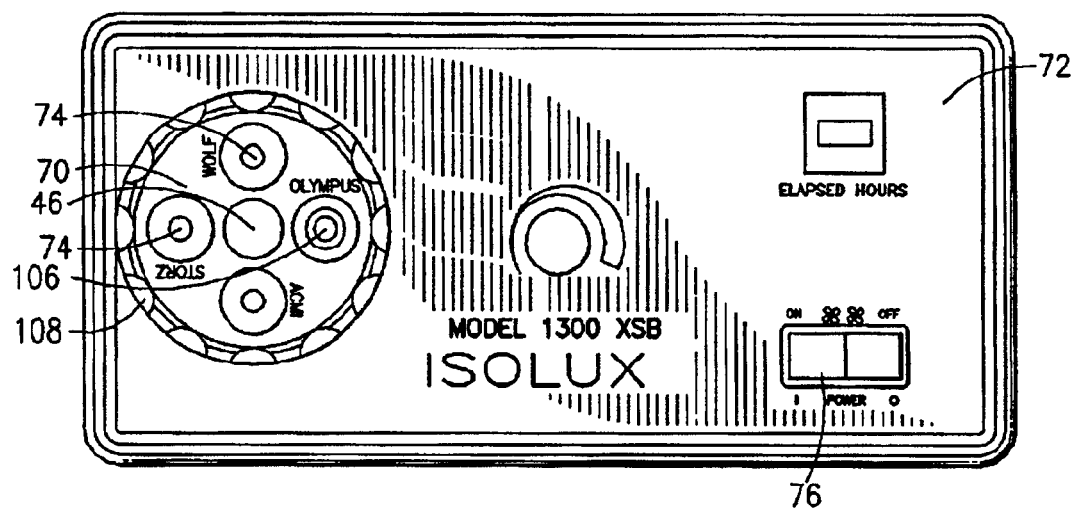
FIG. 5A is a front view of the preferred embodiment of the invention.

In addition, as shown in FIGS. 1, 5 and 6, the turret body 24 is attached to a turret handle 70 at the handle axis 46. The turret handle 70 is attached so that it lies outside the front wall 72 to the illuminator 10. It is preferred that the turret handle 70 is made of a rigid and heat resistant material. Plastic is preferred although metal or another material may be used. Having the turret handle 70 a predetermined distance from the turret body 24 and the light source 12 helps the operator of the illuminator 10 avoid burns. There are openings 74 in the turret handle 70 which correspond to the port cavities 30 in the front end 26 of the turret body 24. As shown in FIG. 5, a corresponding hole 106 is formed in the front wall 72 of the illuminator 10, allowing communication between the outside of the illuminator and a properly positioned predetermined port cavity 30. It is also preferred that convenient power switches 76 are located on the front wall 72 of the illuminator 10.

As shown in FIG. 5, fiber-optic cables may be attached to a predetermined port cavity 30 through an appropriate opening 106 in the front wall 72 of the illuminator 10. Thus, as the turret body 24 is incrementally rotated, it presents a predetermined port cavity 30 in optical communication with the light source 12 through a corresponding opening 74 in the handle 70. It is also preferred that the handle 70 has textural elements 108 to ease the use of the handle 70 by the operator. As further shown in FIG. 5, in an alternative embodiment to this invention, one or two turrets 14 may be used in a particular illuminator 10. Each turret body 24 used in a one or more multiple turret illuminator 10 thus has its own handle 70. As shown, it is preferred that the handle 70 be clearly labeled to show which port cavity 30 is in communication with the light source 12.

Each port cavity 30 is preferably customized so that it may be used with a, different fiber-optic cable. For example, as shown in FIGS. 2, 3, 3A and 4A, 4B and 4C, a port cavity 30a may comprise a shaped spring 78 located in a recess 80 complementary to the spring 78. Preferably the spring 78 is made from a resilient, yet rigid, material, such as stainless steel. The spring 78 may be generally square in shape, as appropriate for adapting the port cavity 30a for attachment to an ACMI fiber-optic cable, or its equivalent.

Figure 4A:
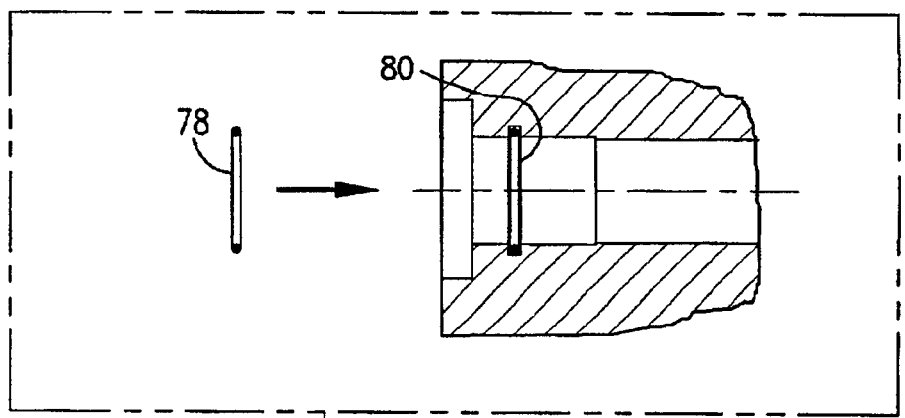
FIG. 4A is a cutaway side view of an embodiment of a port cavity of the invention.
Figure 4B:
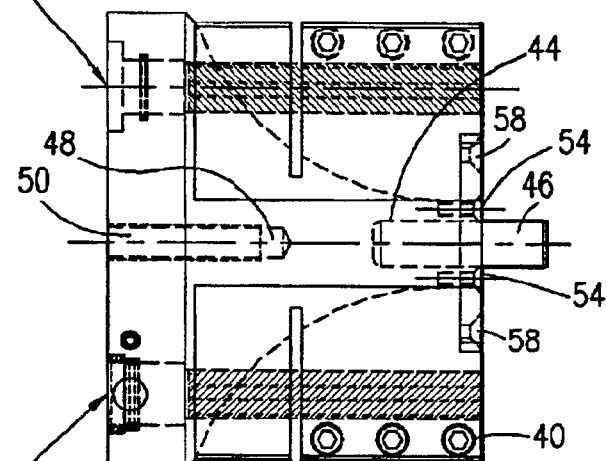
FIG. 4B is a cutaway side view of the turret of the invention.
Figure 4C:
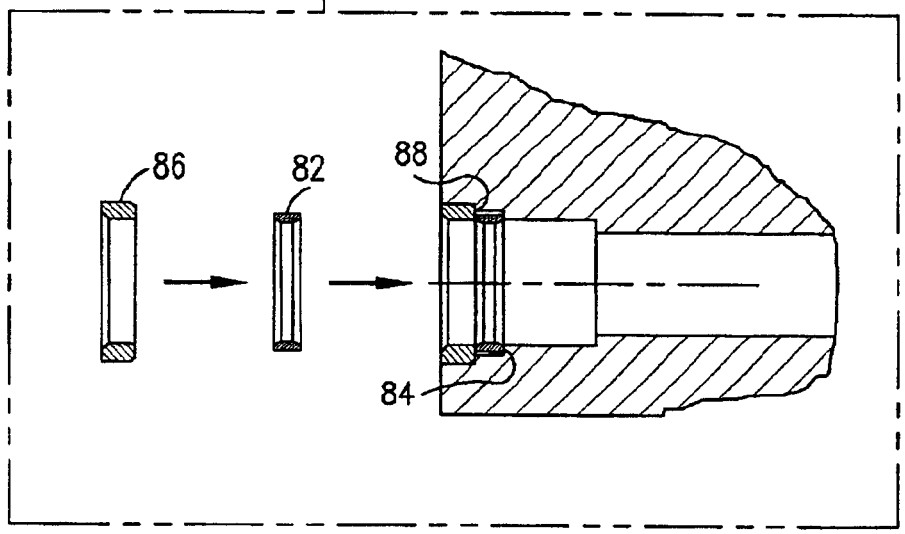
FIG. 4C is a cutaway side view of an alternative embodiment of a port cavity of the invention.

In another example of a port cavity 30b, a differently shaped spring 82 may be located in an appropriate recess 84 for the spring 82. In addition, a bushing 86 may be added and located in an appropriate recess 88 for the bushing 86. As shown in FIG. 4c, the port cavity 30b is thus adaptable for use with a Wolf type fiber-optic cable, or its equivalent.

In still another example of a port cavity 30c, a resilient biased bearing mechanism 90 is used, and placed within an offset chamber 92 located in the front end 26 of the turret body 24. The resilient bearing mechanism 90 preferably comprises a spring retaining mechanism 98 within the offset chamber 92. The biasing means, such as a spring 96 is placed within the spring retaining mechanism 90. A bearing 102 is located between the inner end 100 of the spring 96 and the port cavity 30c. It is preferred that the spring 96 and the bearing 102 are made of stainless steel. A setscrew 110 keeps the spring retaining mechanism 98 in place within the offset chamber 92. In this manner, the port cavity 30c is adaptable for use with a Storz fiber-optic cable, or its equivalent.

In still another alternative port cavity 30d, the perimeter of the front face of the front end 26 of the turret body 24 is contoured. Thus, the port cavity 30d is adaptable for use with an Olympus type fiber-optic cable, or its equivalent.

It will be seen that the objects set forth above, and those made apparent from the foregoing description, are efficiently attained and since certain changes may be made in the above construction without departing from the scope of the invention, it is intended that all matters contained in the foregoing description or shown in the accompany drawings shall be interpreted as illustrative and not in a limiting sense.

It is also to be stood that the following claims are intended to cover all of the generic and specfic features of the invention herein described, and all statements of the scope of the invention which, as a matter of language, might be said to fall therebetween. Now that the invention has been described.

What is claimed is:

1. A rotary indexing turret for interconnecting a fiber-optic illuminator having a light source and a fiber-optic cable for use within a housing for the fiber-optic illuminator, comprising:
    a generally cylindrical body portion with a front end and a back end, having a plurality of openings with ports wherein each port is adapted for inter-engagement with a specific type of fiber-optic cable;
    means for incrementally rotating and indexing the body portion within the housing of the fiber-optic illuminator so that a particular port is in optical communication with the light source including a disk with a front surface and a back surface including a plurality of depressions on the back surface located at the back end of the turret body whereby each depression is adapted to receive a resilient biased bearing located within the housing of the fiber-optic illuminator; and
    means for attaching the disk to the rear portion of the turret body.

2. The turret of claim 1, further comprising one or more cooling fins located around each opening.

3. The turret of claim 1, further comprising:
    a stand axis; and
    a handle axis.

4. The turret of claim 3, further comprising a handle located outside the housing connected to the body portion of the turret at the handle axis.

5. The turret of claim 1, wherein the port further includes a spring adapted for linkage to a specific fiber-optic cable.

6. A rotary indexing turret for interconnecting a fiber-optic illuminator having a light source and a fiber-optic cable for use within a housing for the fiber-optic illuminator, comprising:
    a generally cylindrical body portion with a front end and a back end, having a plurality of openings with ports wherein each port is adapted for inter-engagement with a specific type of fiber-optic cable; and
    means for incrementally rotating and indexing the body portion within the housing of the fiber-optic illuminator so that a particular port is in optical communication with the light source, wherein the means for incrementally rotating and indexing the body portion comprises, a plurality of depressions on the back end of the turret body whereby each depression is adapted to receive a resilient biased bearing located within the housing of the fiber-optic illuminator.

7. The turret of claim 6, further comprising one or more cooling fins located around each opening.

8. The turret of claim 6, further comprising:
    a stand axis; and
    a handle axis.

9. The turret of claim 8, further comprising a handle located outside the housing connected to the body portion of the turret at the handle axis.

10. The turret of claim 6, wherein the port further includes a spring adapted for linkage to a specific fiber-optic cable.

11. A rotary indexing turret for interconnecting a fiber-optic illuminator having a light source and a fiber-optic cable for use within a housing for the fiber-optic illuminator, comprising:
    a generally cylindrical body portion with a front end and a back end, having a plurality of openings with ports wherein each port is adapted for inter-engagement with a specific type of fiber-optic cable;
    one or more cooling fins located around each opening wherein the one or more cooling fins further comprises, a cleft, a tubular lens within the cleft, and means for securing the tubular lens within the cleft; and
    means for incrementally rotating and indexing the body portion within the housing of the fiber-optic illuminator so that a particular port is in optical communication with the light source.

12. The turret of claim 11, further comprising:
    a stand axis; and
    a handle axis.

13. The turret of claim 12, further comprising a handle located outside the housing connected to the body portion of the turret at the handle axis.

14. The turret of claim 11, wherein the port further includes a spring adapted for linkage to a specific fiber-optic cable.

15. A fiber-optic illuminator, comprising:
   a light source;
   a turret comprising a plurality of ports each with a front end and a back end wherein the front end of each port is specifically adapted for inter-engagement with a fiber-optic cable, a disk with a front surface and a back surface including a plurality of depressions on the back surface located at the rear portion of the turret whereby each depression is adapted to receive a resilient biased bearing within the housing of the fiber-optic illuminator and means for attaching the disk to the rear portion of the turret body;
   a housing having an inside and an outside that at least partially encloses the light source and the turret body such that a particular port simultaneously is in optical communication with the light source and is accessible from outside the housing; and
   means for rotatably mounting the turret within the housing such that a particular port simultaneously is in optical communication with the light source and is accessible from outside the housing.

16. The fiber-optic illuminator of claim 15, further comprising a handle located outside the housing connected to a front end of the turret.

17. The fiber-optic illuminator of claim 15, wherein the housing further comprises a stand for the turret located inside the housing.

18. A fiber-optic illuminator, comprising:
   a light source;
   a turret comprising a plurality of ports each with a front end and a back end wherein the front end of each port is specifically adapted for inter-engagement with a fiber-optic cable;
   a housing having an inside and an outside that at least partially encloses the light source and the turret body such that a particular port simultaneously is in optical communication with the light source and is accessible from outside the housing;
   means for rotatably mounting the turret within the housing such that a particular port simultaneously is in optical communication with the light source and is accessible from outside the housing, wherein the means for incrementally rotating the body portion comprises, a plurality of depressions on the back end of the turret body whereby each depression is adapted to receive a resilient biased bearing located within the housing of the fiber-optic illuminator.

19. The fiber-optic illuminator of claim 18, further comprising a handle located outside the housing connected to a front end of the turret.

20. The fiber-optic illuminator of claim 18, wherein the housing further comprises a stand for the turret located inside the housing.

21. A fiber-optic illuminator, comprising:
   a light source;
   a turret comprising a plurality of ports each with a front end and a back end wherein the front end of each port is specifically adapted for inter-engagement with a fiber-optic cable;
   a housing having an inside and an outside that at least partially encloses the light source and the turret body such that a particular port simultaneously is in optical communication with the light source and is accessible from outside the housing, wherein the housing further comprises a stand for the turret located inside the housing, wherein the stand comprises, a depression, a bearing means located at least part way in the depression, and means for resiliently biasing the bearing means so that the bearing is in mechanical cooperation with the turret so that the turret is incrementally rotatable; and
   means for rotatably mounting the turret within the housing such that a particular port simultaneously is in optical communication with the light source and is accessible from outside the housing.

22. A recessed rotary multiple port turret mechanism for mounting within a fiber-optic illumination device, said turret mechanism comprising:
   a turret body adapted for mounting within said fiber-optic illumination device, said turret body comprising a base portion and an elongated portion, said base portion including one or more ports sized to selectively receive and engage an end of one of a multiple of fiber-optic cables, said elongated portion including one or more longitudinal ports disposed therethrough and a plurality of cooling fins longitudinally disposed therethrough, said one or more longitudinal ports corresponding to said one or more ports in said base portion, said one or more longitudinal ports sized to receive and engage said one end of said variety of fiber-optic cables;
   mounting means for mounting said turret body within said illumination device; and
   selective rotating means for selectively controlling the rotation of said turret body in order to expose one of said turret body ports such that light from said illumination device is directed through a corresponding fiber-optic cable engaged with said exposed port.

23. The recessed rotary multiple port turret indexing mechanism of claim 22 wherein each said base portion port is adapted for a different fiber-optic cable.

* * * * *